US012678205B2

(12) United States Patent
Lee

(10) Patent No.: US 12,678,205 B2
(45) Date of Patent: Jul. 14, 2026

(54) SPACING-ADJUSTABLE ORTHOPEDIC APPARATUS

(71) Applicant: KOREA UNIVERSITY RESEARCH AND BUSINESS FOUNDATION, Seoul (KR)

(72) Inventor: Eui Seok Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 470 days.

(21) Appl. No.: 18/262,189

(22) PCT Filed: Jan. 18, 2022

(86) PCT No.: PCT/KR2022/000867
§ 371 (c)(1),
(2) Date: Jan. 18, 2024

(87) PCT Pub. No.: WO2022/158812
PCT Pub. Date: Jul. 28, 2022

(65) Prior Publication Data
US 2025/0275792 A1　Sep. 4, 2025

(30) Foreign Application Priority Data

Jan. 19, 2021　(KR) ........................ 10-2021-0007383
Feb. 10, 2021　(KR) ........................ 10-2021-0018780

(51) Int. Cl.
*A61B 17/80*　(2006.01)
*A61B 17/86*　(2006.01)
(Continued)

(52) U.S. Cl.
CPC ...... *A61B 17/8009* (2013.01); *A61B 17/8071* (2013.01); *A61B 17/8605* (2013.01);
(Continued)

(58) Field of Classification Search
CPC ........... A61B 17/8004; A61B 17/8009; A61B 17/8014; A61B 17/8023; A61B 17/8071; A61B 17/7055; A61B 17/7071
See application file for complete search history.

(56) References Cited

U.S. PATENT DOCUMENTS

2012/0197303 A1* 8/2012 King .................. A61B 17/1728
606/282
2015/0230838 A1* 8/2015 Lazoglu ............. A61B 17/8004
606/71

FOREIGN PATENT DOCUMENTS

JP　2007-151674 A　6/2007
KR　10-1210089 B1　12/2012
KR　10-2018-0011499 A　2/2018

OTHER PUBLICATIONS

International Search Report for PCT/KR2022/000867 by Korean Intellectual Property Office dated May 9, 2022.

* cited by examiner

*Primary Examiner* — Andrew Yang
(74) *Attorney, Agent, or Firm* — BROADVIEW IP LAW, PC

(57) ABSTRACT

The present invention relates to a spacing-adjustable bone orthopedic apparatus. The apparatus may include a plate including a main body and a through portion having a predetermined length and formed to pass through the main body and a locking screw which is inserted into the through portion, which includes a screw body and a screw head which are capable of being coupled to each other, and in which outer circumferential surface saw teeth are formed on an outer circumferential surface of the screw head.

14 Claims, 11 Drawing Sheets

(51) Int. Cl.
*A61B 17/00*        (2006.01)
*A61B 17/68*        (2006.01)
(52) U.S. Cl.
CPC ...... *A61B 17/8625* (2013.01); *A61B 17/8685*
(2013.01); *A61B 17/8695* (2013.01); *A61B*
*2017/00398* (2013.01); *A61B 2017/00477*
(2013.01); *A61B 2017/00862* (2013.01); *A61B*
*2017/681* (2013.01)

(a)

(b)

SPACING-ADJUSTABLE ORTHOPEDIC APPARATUS

TECHNICAL FIELD

The present invention relates to a spacing-adjustable bone orthopedic apparatus for adjusting the relative positions of two bone fragments during bone orthopedic surgery.

BACKGROUND ART

Generally, a mandibular fixation plate is an auxiliary medical device used, after a part of a jawbone is removed or incised when performing facial cosmetic surgery for a chin for correcting a protruding chin or oral cancer surgery or after an abnormal portion is found in a bone and the abnormal portion is removed, to maintain a shape of the remaining portion or transplant and fix it with new bone.

Hereinafter, a conventional method of applying a mandibular fixation plate to the mandible of a face will be described with reference to FIGS. 1 and 2 as follows.

FIG. 1 is a is a perspective view illustrating a conventional fixation plate for mandibular surgery, and FIG. 2 is a perspective view illustrating the fixation plate for mandibular surgery of FIG. 1 attached to the mandible.

Referring to FIGS. 1 and 2, in a state in which a part of the mandible is removed or incised, the fixation plate for mandibular surgery is mounted on a front surface of the mandible, and a conventional plate body 1 for mandibular surgery is formed of a material with a predetermined strength or more. A plurality of ring-shaped fixing parts 2 in which through portions 3 are formed at equal intervals are formed in the plate body 1. Screws 4 are inserted into the mandible through the through portions 3, and thus the plate body 1 is fastened to the mandible. The fixing parts 2 are mutually connected through connecting parts 5, and tapered surfaces 6 for allowing head portions of the fastened screws 4 to be seated are formed on inner circumferential surfaces of the fixing parts 2.

An operator inserts the screws 4 into the through portions 3 formed in the fixing parts 2 and then fastens the screws 4 to the mandible to complete a joining surgical procedure of the incised mandible.

Meanwhile, during the joining surgical procedure of the mandible, since a patient is under anesthesia, and the patient has not sensation, consciousness, and muscle activity, in a state in which a head is fixed using a tool, the fixation plate is fixed while the mandible is positioned according to the operator's experience.

However, as a position of the fixation plate slightly is changed in upward, downward, left, and right directions for each patient after the surgical procedure is performed due to a different growth rate and a growth direction of the mandible, a tooth structure, and chewing habits, the position of the conventional mandibular fixation plate needs to be finely adjusted. However, when the position of the conventional fixation plate is adjusted, a fastening state of the screws 4 fastened to the through portions 3 of the fixing parts 2 formed in the plate body 1 is released and then the screws 4 should be fixed to new positions, and thus there is a problem that it is actually very difficult to adjust the position of the fixation plate.

RELATED ART

Patent Document (Patent Document 1) Korean Registered Patent No. 10-1210089

Technical Problem

The present invention is directed to providing a spacing-adjustable bone orthopedic apparatus capable of finely adjusting the relative positions of two bone fragments after surgery.

Technical Solution

One aspect of the present invention provides a spacing-adjustable bone orthopedic apparatus, and the apparatus includes a plate including a main body and a through portion having a predetermined length and formed to pass through the main body and a locking screw which is inserted into the through portion, which includes a screw body and a screw head which are capable of being coupled to each other, and in which outer circumferential surface saw teeth are formed on an outer circumferential surface of the screw head.

According to a first embodiment of the present invention, the plate may include a sidewall formed at one side of the main body, a plurality of plate saw teeth may be formed on the sidewall in a longitudinal direction of the sidewall to extend toward the through portion, the screw body may include a body portion in which a screw thread is formed on a lower outer circumferential surface of the screw body and a head portion in which locking saw teeth are formed on an upper outer circumferential surface of the screw body, the outer circumferential surface saw teeth of the screw head may correspond to a shape of the plate saw teeth, and inner circumferential surface saw teeth corresponding to a shape of the locking saw teeth of the head portion of the screw body may be formed on a part of an inner circumferential surface of the screw head.

According to the first embodiment of the present invention, the screw head may be disposed on the through portion and supported by an upper surface of the main body of the plate.

According to the first embodiment of the present invention, the inner circumferential surface of the screw head may include a locking region in which the inner circumferential surface saw teeth are formed and a locking release region other than the locking region, wherein the locking region may be formed to extend inside the inner circumferential surface of the screw head and has a predetermined height.

According to the first embodiment of the present invention, it may be designed that a locking protrusion protruding inward is formed on a portion adjacent to a lowermost side of the inner circumferential surface of the screw head and a lower side surface of the head portion of the screw body is caught by the locking protrusion.

According to the first embodiment of the present invention, the spacing-adjustable bone orthopedic apparatus may further include an elastic member which is disposed between a lower surface of the screw head and the main body and of which one side is inclined toward the lower surface of the screw head.

According to the first embodiment of the present invention, the elastic member may be a spring washer.

According to the first embodiment of the present invention, the spacing-adjustable bone orthopedic apparatus may further include head rachet saw teeth formed on a lower side surface of the screw head and body rachet saw teeth formed on an upper side surface of the main body and corresponding to a shape of the head rachet saw teeth.

According to the first embodiment of the present invention, the locking screw may include a first locking screw and a second locking screw disposed in the through portion to be spaced apart from the first locking screw in a longitudinal direction of the through portion.

According to the first embodiment of the present invention, a screw fixing hole spaced apart from the through portion may be formed in the plate.

According to a second embodiment of the present invention, the plate may include a first support part and a second support part which are formed to protrude from a bottom surface at one side of the main body and are spaced apart from each other, wherein the spacing-adjustable bone orthopedic apparatus may include a worm which is supported by the first support part and the second support part and on which a screw thread that engages with the outer circumferential surface saw teeth of the locking screw is formed, and the locking screw may be used as a worm wheel.

According to the second embodiment of the present invention, one end portion of the worm may pass through and may be supported by the first support part, and the other end portion of the worm may pass through and may be supported by the second support part.

According to the second embodiment of the present invention, the spacing-adjustable bone orthopedic apparatus may further include a motor which is connected to the worm and rotates the worm in one direction or the other direction.

According to the second embodiment of the present invention, the plate may further include a sidewall formed at the other side of the main body, and a plurality of plate saw teeth that are disposed in front of the worm and engage with the outer circumferential surface saw teeth of the locking screw may be formed on the sidewall in a longitudinal direction.

According to the second embodiment of the present invention, the spacing-adjustable bone orthopedic apparatus may further include a second locking screw disposed in the through portion to be spaced apart from the locking screw, wherein the second locking screw may engage with the plate saw teeth and move in a longitudinal direction of the through portion.

Advantageous Effects

According to the present invention, the relative positions of two bone fragments can be easily finely adjusted after surgery by using a locking screw of which a locking state or a locking release state can be selectively set and which can perform both a function of moving a bone fragment and a function of fixing a plate to the bone fragment.

In addition, the relative positions of two bone fragments can be finely adjusted after surgery by rotating a locking screw using a worm.

MODES OF THE INVENTION

Hereinafter, specific content for implementing the present invention will be described with reference to the accompanying drawings. In addition, in description of the present invention, when it is determined that detailed description of related well-known functions which are obvious to those skilled in the art may unnecessarily obscure the gist of the present invention, such detailed description will be omitted.

A first embodiment of a spacing-adjustable bone orthopedic apparatus according to the present invention will be described below.

Figure 1:
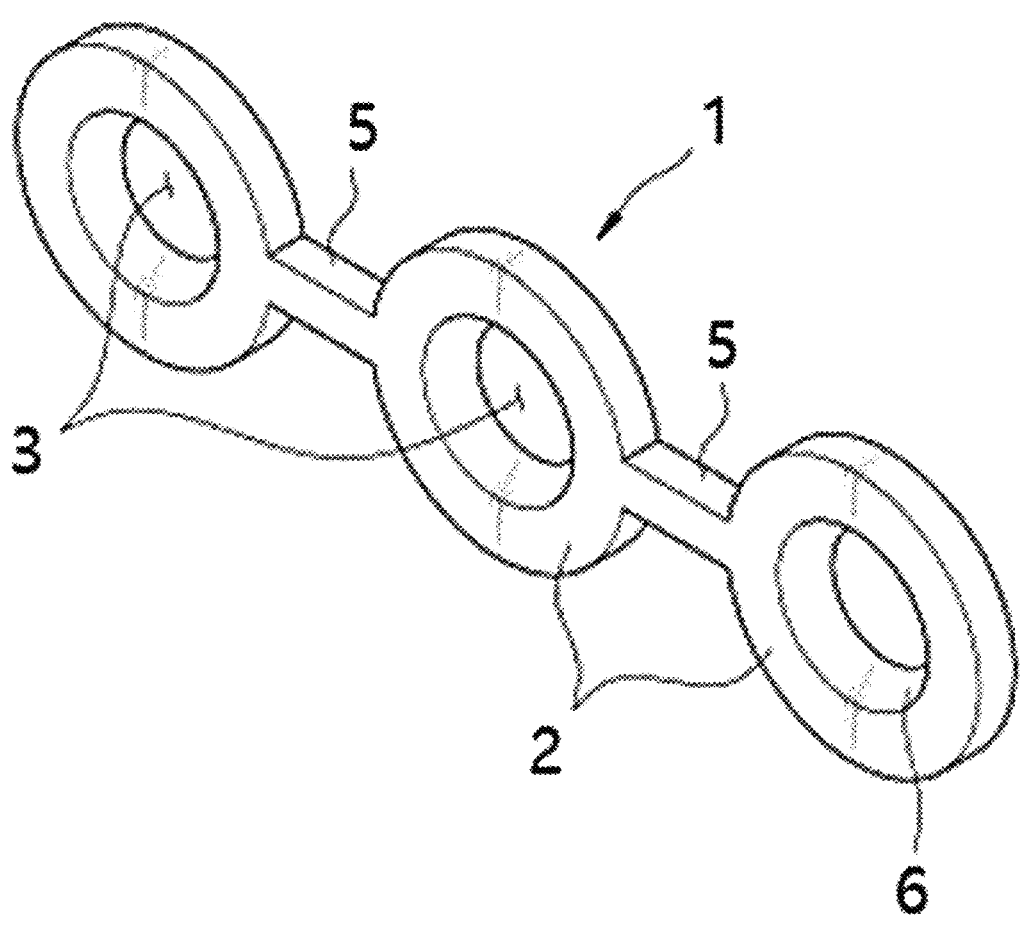
FIG. 1 is a perspective view illustrating a conventional fixation plate for mandibular surgery.
Figure 2:
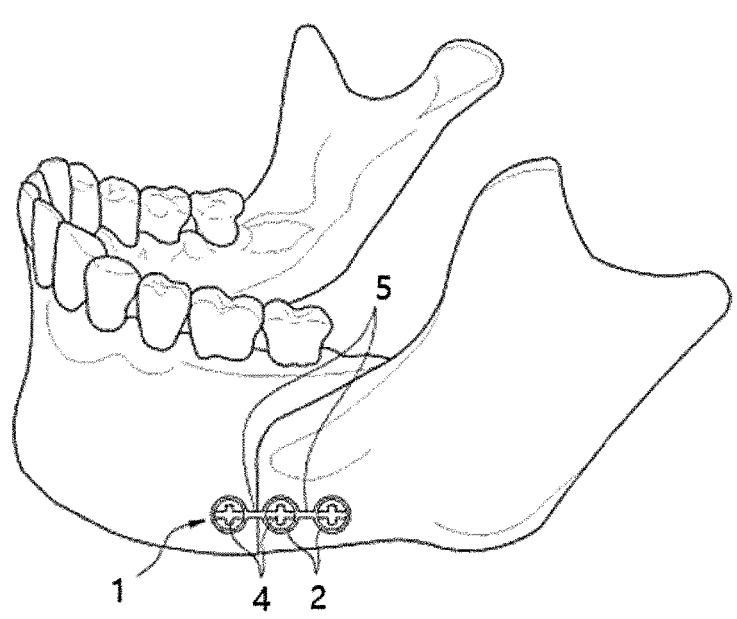
FIG. 2 is a perspective view illustrating a state in which the fixation plate for mandibular surgery of FIG. 1 is attached to the mandible.
Figure 3:
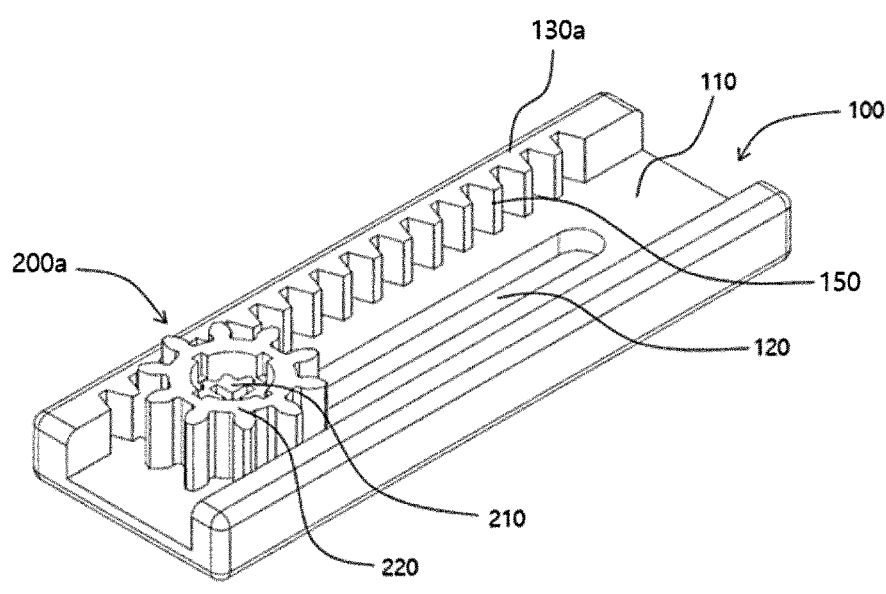
FIG. 3 is a perspective view illustrating a locking screw mounted on a plate in a spacing-adjustable bone orthopedic apparatus according to a first embodiment of the present invention.
Figure 4:
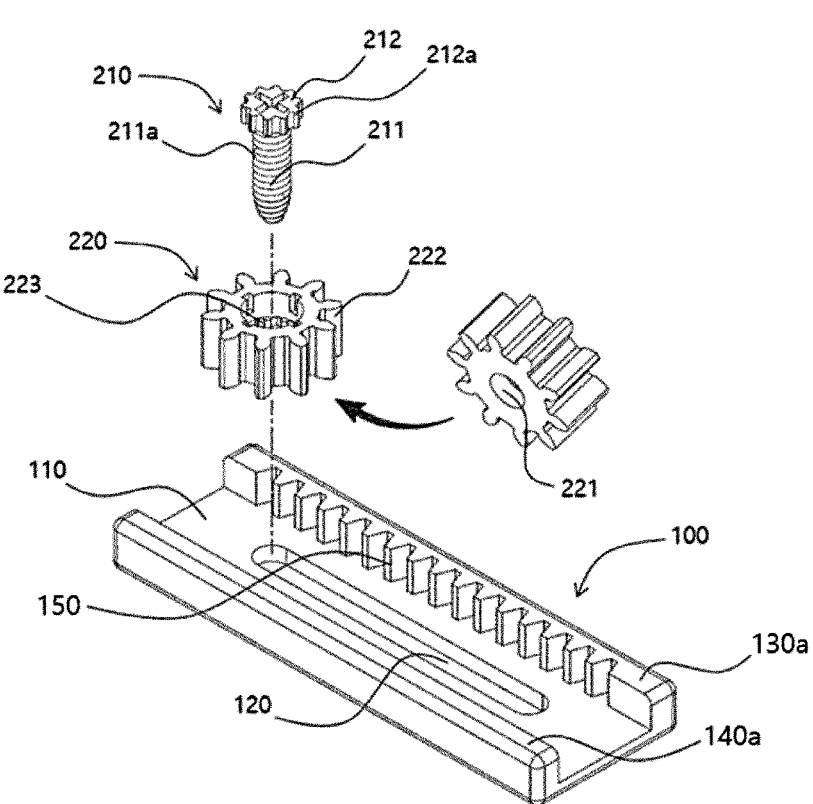
FIG. 4 is an exploded view illustrating the spacing-adjustable bone orthopedic apparatus of FIG. 3.

FIG. 3 is a perspective view illustrating a locking screw mounted on a plate in a spacing-adjustable bone orthopedic apparatus according to a first embodiment of the present invention. FIG. 4 is an exploded view illustrating the spacing-adjustable bone orthopedic apparatus of FIG. 3.

Referring to FIGS. 3 and 4, the spacing-adjustable bone orthopedic apparatus according to the present invention includes a plate 100 and a locking screw 200a.

The plate 100 includes a main body 110, a through portion 120 having a predetermined length and formed to pass through a central portion of the main body 110, and a sidewall 130*a* formed at one side of the main body 110. A plurality of plate saw teeth 150 extending toward the through portion 120 in a longitudinal direction of the sidewall 130*a* are formed on the sidewall 130*a*.

The plate 100 is disposed across a first bone and a second bone, which are two adjacent bone fragments, one side surface of the main body 110 of the plate 100 is supported by an upper surface of the first bone, and the other side surface thereof is supported by an upper surface of the second bone. Since the first bone and the second bone are spaced apart from each other, a certain region of the central portion of the main body 110 is a region which is not in contact with either the first bone or the second bone.

The through portion 120 has an elliptical shape formed to extend in a longitudinal direction of the main body 110. The through portion 120 is spaced a predetermined distance from the sidewall 130*a* and oriented parallel to the sidewall 130*a*. One side of the through portion 120 is disposed on the first bone, and the other side thereof is disposed on the second bone. A width of the through portion 120 is greater than a diameter of a body portion 211 of a screw body 210 and smaller than a diameter of a head portion 212 of the screw body 210.

The plurality of plate saw teeth 150 are formed on the sidewall 130*a*, and a second sidewall 140*a* faces the sidewall 130*a* and is formed at the other side of the plate 100. The sidewall 130*a* and the second sidewall 140*a* are formed to extend upward from one end portion and the other end portion of the plate, respectively. A distance between the second sidewall 140*a* and a longitudinal axis of the through portion 120 is greater than a distance between the sidewall 130*a* and the longitudinal axis of the through portion 120. The distance between the sidewall 130*a* and the longitudinal axis of the through portion 120 is approximately a radius of the screw head 220 of the locking screw 200*a*. A height of the sidewall 130*a* and a height of the second sidewall 140*a* may be the same as a height of the screw head 220.

The plate saw teeth 150 have a length greater than a length of the through portion 120 and are formed to extend in a longitudinal direction of an inner side surface of the sidewall 130*a*. A height of the extending plate saw teeth 150 may be the same as a height of extending outer circumferential surface saw teeth 222 formed on an outer circumferential surface of the screw head 220.

The locking screw 200*a* is inserted into the through portion 120. The locking screw 200*a* includes the screw body 210 and the screw head 220 which are capable of being coupled to each other. A hollow which is greater than the diameter of the head portion 212 of the screw body 210 is formed in the screw head 220 so that the screw body 210 may be inserted into the screw head 220. In a state in which the screw head 220 is disposed on the through portion 120 and fixed to the main body 110 of the plate 100, the screw body 210 may be inserted into the first or second bone through the through portion 120 and coupled to an inner portion of the hollow of the screw head 220.

The screw body 210 includes the body portion 211 in which a screw thread 211*a* is formed on a lower outer circumferential surface of the screw body 210 and the head portion 212 in which locking saw teeth 212*a* are formed on an upper outer circumferential surface of the screw body 210. While the body portion 211 of the screw body 210 passes through the through portion 120 and is inserted into the first or second bone, a screw groove corresponding to the screw thread 211*a* is formed in the first or second bone by the screw thread 211*a* and engages with the screw thread 211*a* formed on the body portion 211. An insertion groove

212*b* into which a driver or the like is inserted is formed in an upper surface of the head portion 212 of the screw body 210. A user may insert the driver or the like into the insertion groove 212*b* and rotate the driver to insert the screw body 210 into the first or second bone.

The screw head 220 is disposed on the through portion 120 and supported by an upper surface of the main body 110 of the plate 100. The screw head 220 may be disposed between the sidewall 130*a* and the second sidewall 140*a* and may have the same height as the height of each of the sidewall 130*a* and the second sidewall 140*a*.

A locking protrusion 221 protruding inward is formed on a portion adjacent to a lowermost side of an inner circumferential surface of the screw head 220. While the screw body 210 is inserted into the first or second bone, a lower side surface of the head portion 212 of the screw body 210 is caught by the locking protrusion 221 of the screw head 220. The locking protrusion 221 extends to a length such that the head portion 212 of the screw body 210 is supported and the locking protrusion 221 does not come into contact with the body portion 211 of the screw body 210. The head portion 212 of the screw body 210 is caught by the locking protrusion 221 and is not inserted further downward.

The outer circumferential surface saw teeth 222 corresponding to a shape of the plate saw teeth 150 are formed on the outer circumferential surface of the screw head 220. The outer circumferential surface saw teeth 222 are formed along a circumference of a circumferential surface of the screw head 220. The outer circumferential surface saw teeth 222 may be formed to move in the longitudinal direction of the through portion 120 according to a set gear ratio when the screw head 220 rotates while engaging with the plate saw teeth 150.

Figure 5:
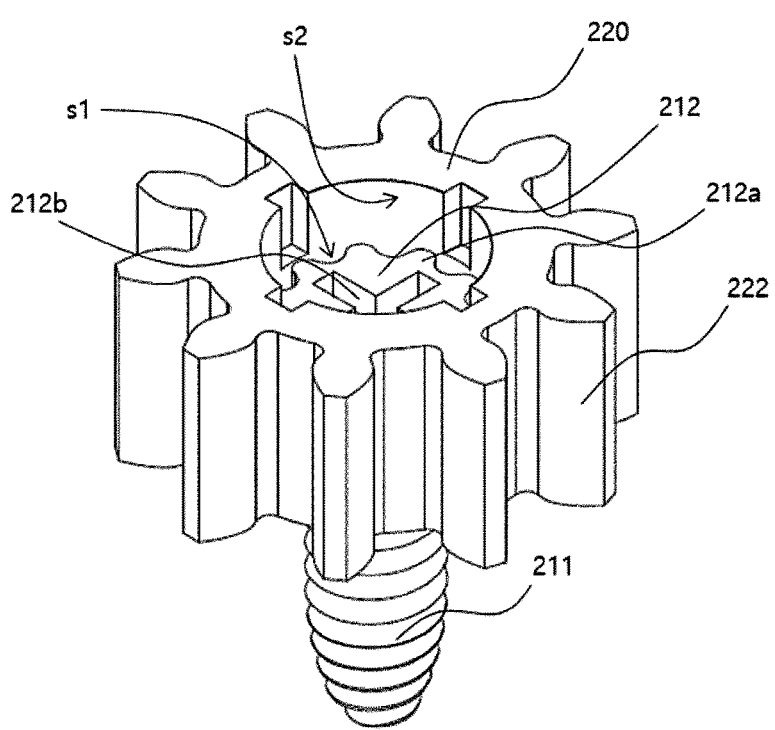
FIG. 5 is a perspective view illustrating a locking state in which a screw body is engaged with a screw head in the locking screw of FIG. 3.
Figure 6:
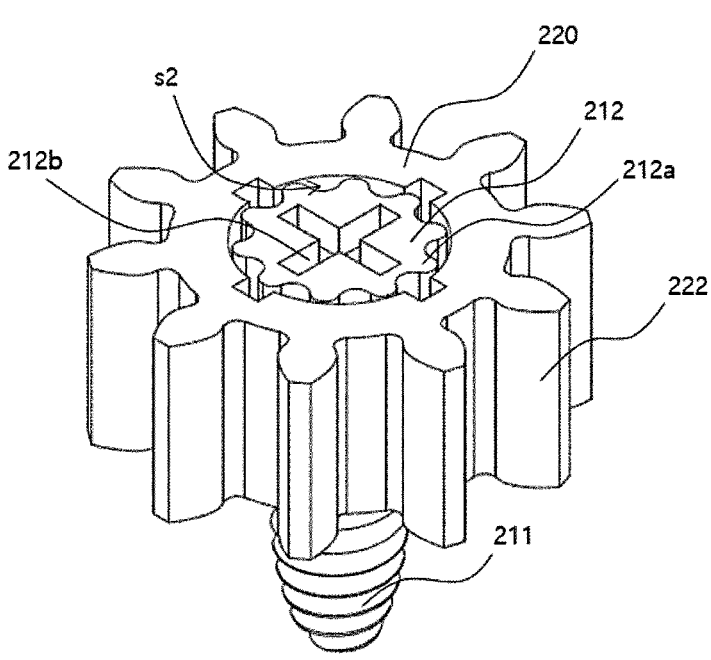
FIG. 6 is a perspective view illustrating a locking release state in which a state in which the screw body is engaged with the screw head in FIG. 3 is released.

FIG. 5 is a perspective view illustrating a locking state in which the screw body is engaged with the screw head in the locking screw of FIG. 3. FIG. 6 is a perspective view illustrating a locking release state in which a state in which the screw body is engaged with the screw head in FIG. 3 is released.

Referring to FIGS. 5 and 6, inner circumferential surface saw teeth 223 corresponding to a shape of the locking saw teeth 212*a* of the head portion 212 of the screw body 210 are formed on a part of the inner circumferential surface of the screw head 220. The inner circumferential surface saw teeth 223 are formed along a circumference of a part of the inner circumferential surface of the screw head 220. The inner circumferential surface saw teeth 223 may be formed on a lower region of the inner circumferential surface of the screw head. A height of the extending inner circumferential surface saw teeth 223 may be the same as a height of the extending locking saw teeth 212*a* of the head portion 212 of the screw body 210. The inner circumferential surface saw teeth 223 are formed to engage with the locking saw teeth 212*a* of the head portion 212 of the screw body 210 while the screw head 220 moves upward or downward with respect to the screw body 210.

In the inner circumferential surface of the screw head 220, a region in which the inner circumferential surface saw teeth 223 are formed is referred to as a locking region s1, and a region other than the locking region s1 is referred to as a locking release region s2. The inner circumferential surface saw teeth 223 are formed in only the locking region s1 of a part of the inner circumferential surface of the screw head 220. Accordingly, since a height of the screw body 210 is changed in the hollow of the screw head 220, a locking state in which the inner circumferential surface saw teeth 223 and the locking saw teeth 212*a* are engaged and a locking release state in which the inner circumferential surface saw teeth 223 and the locking saw teeth 212a are not engaged may be selectively formed. Meanwhile, a plurality of rotation grooves 225 into which an insertion tool (not shown) is inserted are formed in the inner circumferential surface of the screw head 220 in the locking release region s2 in a longitudinal direction. The screw head 220 may be moved downward by inserting the insertion tool into the rotation groove 225 and pressing the insertion tool. In addition, the screw head 220 may be rotated by inserting the insertion tool into the rotation groove 225 and rotating the insertion tool.

When the inner circumferential surface saw teeth 223 are formed on a lower portion of the inner circumferential surface of the screw head 220, while the screw head 220 moves upward, the locking state in which the locking saw teeth 212a of the screw body 210 are engaged with the inner circumferential surface saw teeth 223 of the screw head 220 is formed. Meanwhile, while the screw head 220 moves downward, the locking release state in which a state in which the locking saw teeth 212a of the screw body 210 are engaged with the inner circumferential surface saw teeth 223 of the screw head 220 is released is formed.

Figure 7:
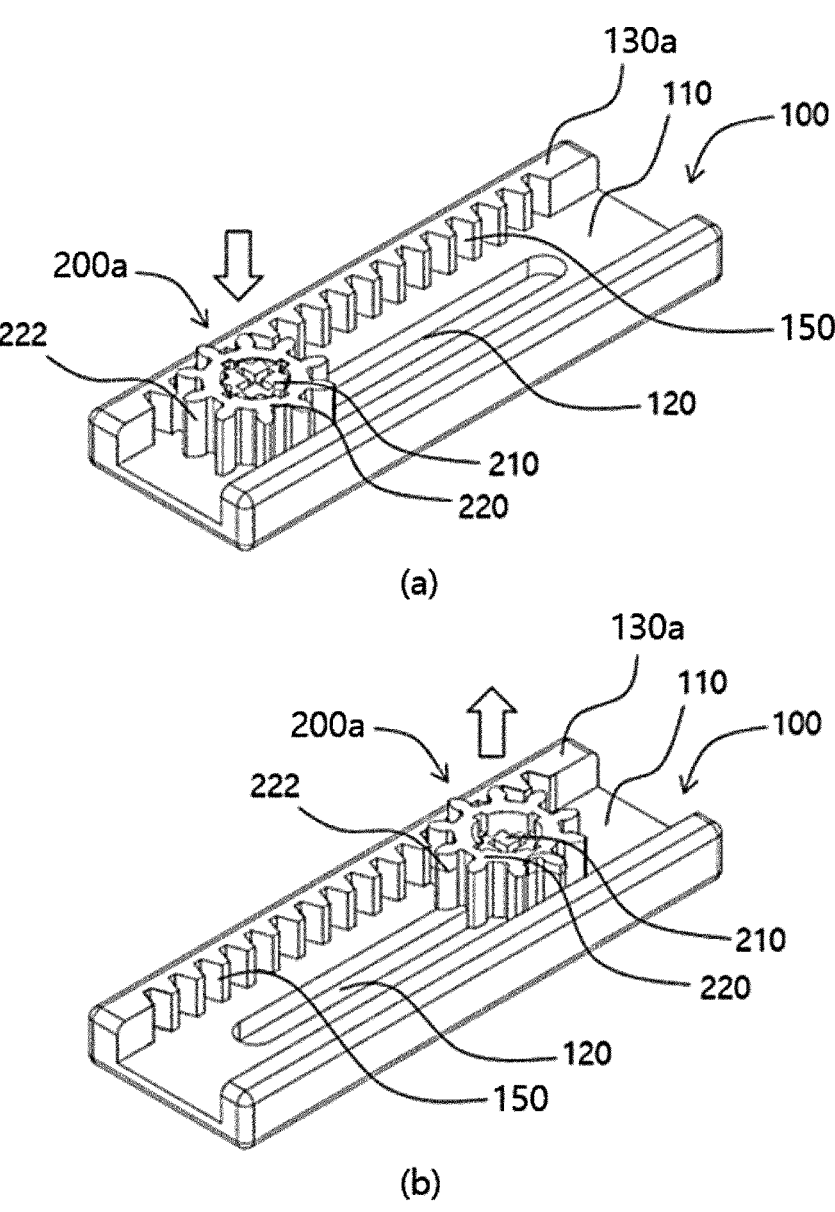
FIG. 7 is a set of perspective views illustrating an operating process of the spacing-adjustable bone orthopedic apparatus according to the first embodiment of the present invention.

FIG. 7 is a set of perspective views illustrating an operating process of the spacing-adjustable bone orthopedic apparatus according to the first embodiment of the present invention.

Referring to FIG. 7, a surgical procedure using the spacing-adjustable bone orthopedic apparatus according to the present invention includes a preparation operation, a screw body insertion operation, a screw head push operation, a screw head rotation operation, and a screw head raising operation. Vertical movement or rotational movement is selectively applied to the screw head 220. In this case, the operator may directly push or rotate the screw head 220 using a tool. Alternatively, vertical movement or rotational movement of the screw head 220 may be controlled using a driving part including a motor.

In the preparation operation, the operator arranges the plate 100 on both the first bone and the second bone so that one side of the plate 100 is in contact with a surface of the first bone and the other side of the plate 100 is in contact with the upper surface of the second bone. In this case, the screw head 220 is mounted on the plate 100.

In the screw body insertion operation, the operator inserts the screw body 210 through the hollow of the screw head 220 and the through portion 120 of the plate 100 and inserts and fixes the body portion 211 of the screw body 210 into the first or second bone. In this case, the head portion 212 of the screw body is caught and fixed on the locking protrusion 221.

In a case in which the inner circumferential surface saw teeth 223 are formed on a lower portion of the inner circumferential surface of the screw head 220, while the screw body 210 moves downward in the hollow of the screw head 220, the locking state in which the locking saw teeth 212a of the screw body 210 are engaged with the inner circumferential surface saw teeth 223 of the screw head 220 is formed (see FIG. 5).

In the screw head push operation, when the screw head 220 moves downward, the head portion 212 of the screw body 210 is positioned in an upper portion of the hollow of the screw head 220. Accordingly, the locking release state in which engagement between the locking saw teeth 212a of the screw body 210 and the inner circumferential surface saw teeth 223 of the screw head 220 is released is formed (see FIG. 6).

In the screw head rotation operation, the screw head 220 is rotated in one or the other direction to move to one side or the other side in the longitudinal direction of the through portion 120. Although the engagement between the screw body 210 inserted into the hollow of the screw head 220 and the screw head 220 is released, the screw body 210 moves with the movement of the screw head 220. A distance between the first bone and the second bone increases or decreases according to a rotational direction of the screw head 220 to adjust a distance between the first bone and the second bone.

In the screw head raising operation, the screw head 220 may naturally move upward due to the inherent elasticity of bone. Accordingly, when the locking saw teeth 212a of the screw body 210 engage with the inner circumferential surface saw teeth 223 of the screw head 220, the locking release state is switched to the locking state. In the locking state, since the screw body 210 is fixed to the first bone or second bone, the screw head 220 engaged with the screw body 210 does not easily move along the plate saw teeth 150 of the plate 100. Due to the inherent elasticity of bone, the screw head 220 may move upward about 0.5 mm to 3 mm.

Figure 8:
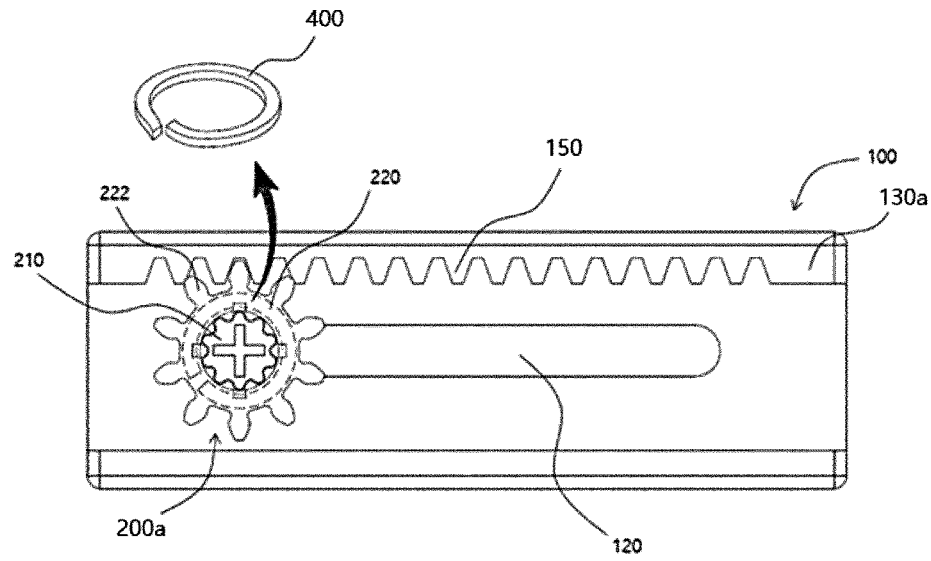
FIG. 8 is a perspective view illustrating an example in which an elastic member for assisting an upward force of the screw head is additionally mounted on the spacing-adjustable bone orthopedic apparatus of FIG. 3.

FIG. 8 is a perspective view illustrating an example in which an elastic member for assisting an upward force of the screw head is additionally mounted on the spacing-adjustable bone orthopedic apparatus of FIG. 3.

Referring to FIG. 8, the spacing-adjustable bone orthopedic apparatus according to the embodiment of the present invention may include an elastic member 400 which is disposed between a lower surface of the screw head 220 and the main body 110 and of which one side is inclined toward the lower surface of the screw head 220. The elastic member 400 may be a washer, that is, a spring washer, which extends obliquely from one end portion to the other end portion and in which a height of one end portion and a height of the other end portion are different. Accordingly, the elastic member 400 may provide an additional upward force in addition to the inherent elasticity of bone.

Figure 9:
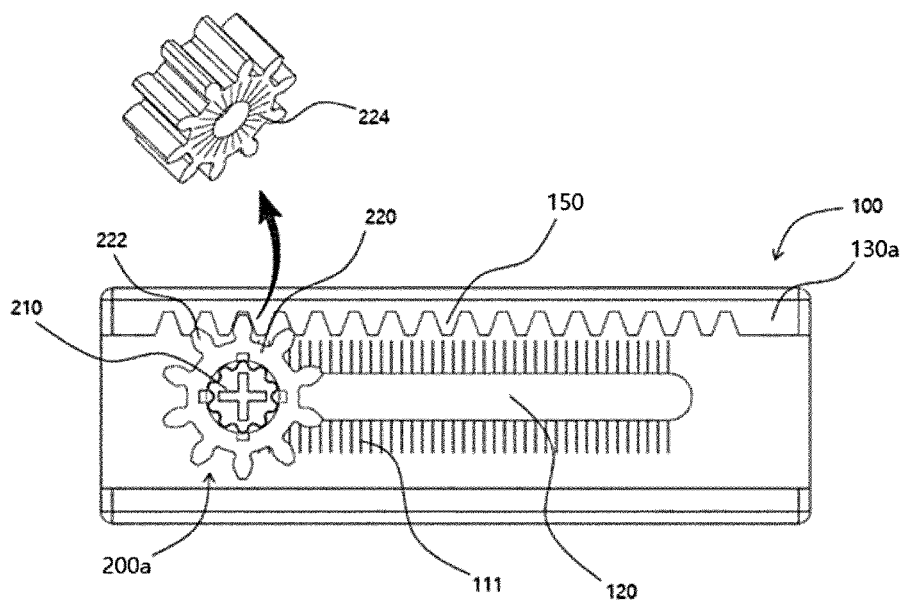
FIG. 9 is a perspective view illustrating an application example in which a ratchet method is applied to the spacing-adjustable bone orthopedic apparatus of FIG. 3.

FIG. 9 is a perspective view illustrating an application example in which a ratchet method is applied to the spacing-adjustable bone orthopedic apparatus of FIG. 3.

Referring to FIG. 9, the spacing-adjustable bone orthopedic apparatus according to the first embodiment of the present invention may include head rachet saw teeth 224 formed on the lower side surface of the screw head 220 and body rachet saw teeth 111 which are formed on the upper side surface of the main body 110 and correspond to a shape of the head rachet saw teeth 224. When the screw head 220 rotates, the head rachet saw teeth 224 of the screw head 220 engage with the body rachet saw teeth 111 of the main body 110. Accordingly, whenever the screw head 220 rotates, a click sound is generated, a frictional force may be provided to the screw head 220 to precisely control the rotation of the screw head 220, and the screw head 220 may also be prevented from idling on the main body 110 when stopped.

Figure 10:
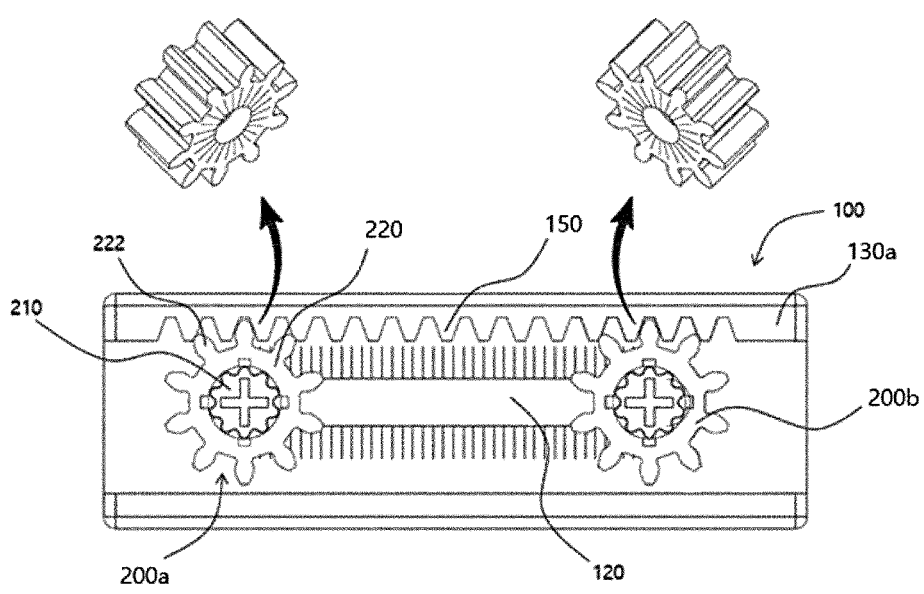
FIG. 10 is a plan view illustrating an example in which the spacing-adjustable bone orthopedic apparatus of FIG. 3 includes two locking screws.

FIG. 10 is a plan view illustrating an example in which the spacing-adjustable bone orthopedic apparatus of FIG. 3 includes two locking screws.

Referring to FIG. 10, the spacing-adjustable bone orthopedic apparatus according to the embodiment of the present invention may include a first locking screw 200a and a second locking screw 200b. The second locking screw 200b is disposed in the through portion 120 to be spaced apart from the first locking screw 200a in the longitudinal direction of the through portion 120. The first locking screw 200a is disposed on the upper side of the first bone, and the second locking screw 200b is disposed on the upper side of the second bone. Accordingly, in a state in which a position of the second locking screw 200*b* is fixed with respect to the second bone, the first locking screw 200*a* may be operated to adjust the movement of the first bone, and in a state in which a position of the first locking screw 200*a* is fixed with respect to the first bone, the second locking screw 200*b* may be operated to adjust the movement of the second bone.

Figure 11:
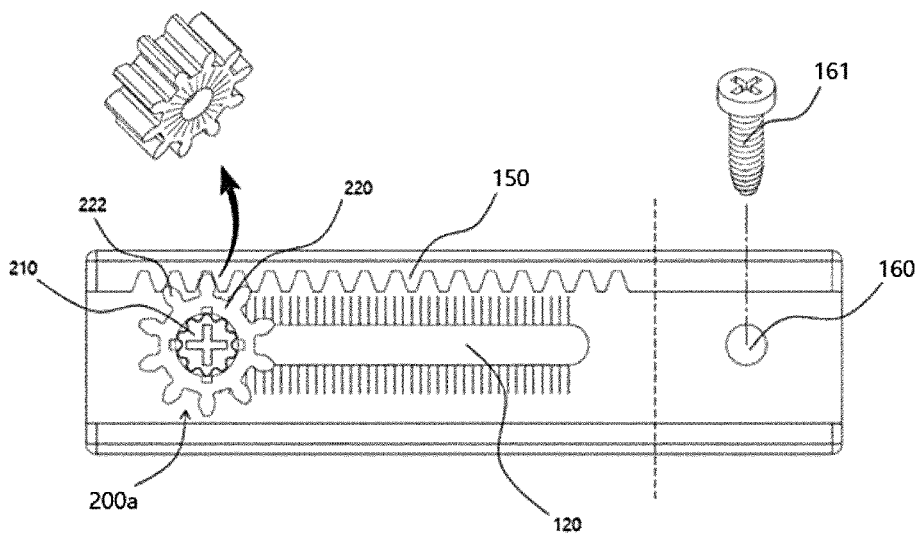
FIG. 11 is a plan view illustrating an application example in which a separate screw fixing hole is formed in the spacing-adjustable bone orthopedic apparatus of FIG. 3.

FIG. 11 is a plan view illustrating an application example in which a separate screw fixing hole is formed in the spacing-adjustable bone orthopedic apparatus of FIG. 3.

Referring to FIG. 11, in the plate 100 of the spacing-adjustable bone orthopedic apparatus according to the embodiment of the present invention, a screw fixing hole 160 spaced apart from the through portion 120 may be formed. In a state in which the plate 100 is fixed to the first or second bone using the screw fixing hole 160 and a fixing screw 161, the locking screw 200*a* may be operated. Accordingly, a fixing force of the plate 100 increases so that a more stable surgical procedure may be performed.

A second embodiment of a spacing-adjustable bone orthopedic apparatus according to the present invention will be described below.

Figure 12:
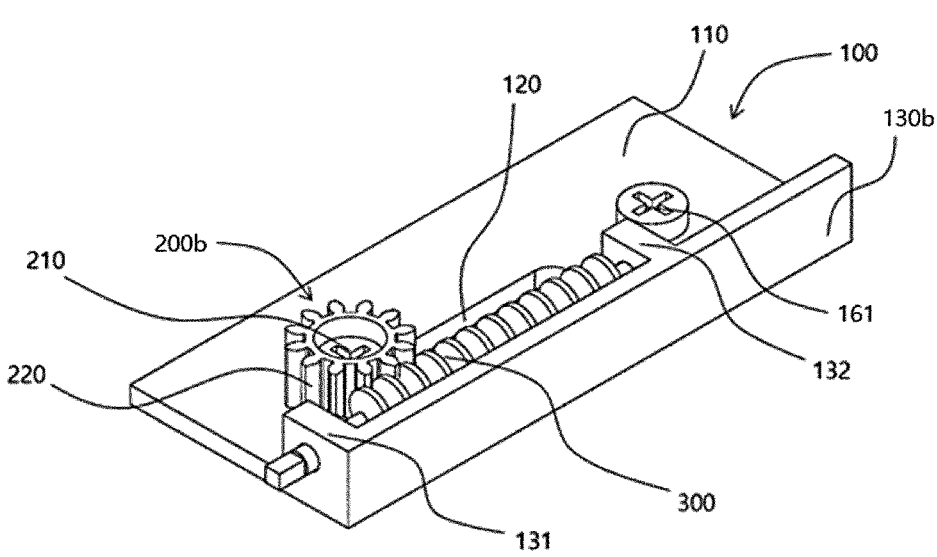
FIG. 12 is a perspective view illustrating a locking screw engaged with a worm in a spacing-adjustable bone orthopedic apparatus according to a second embodiment of the present invention.
Figure 13:
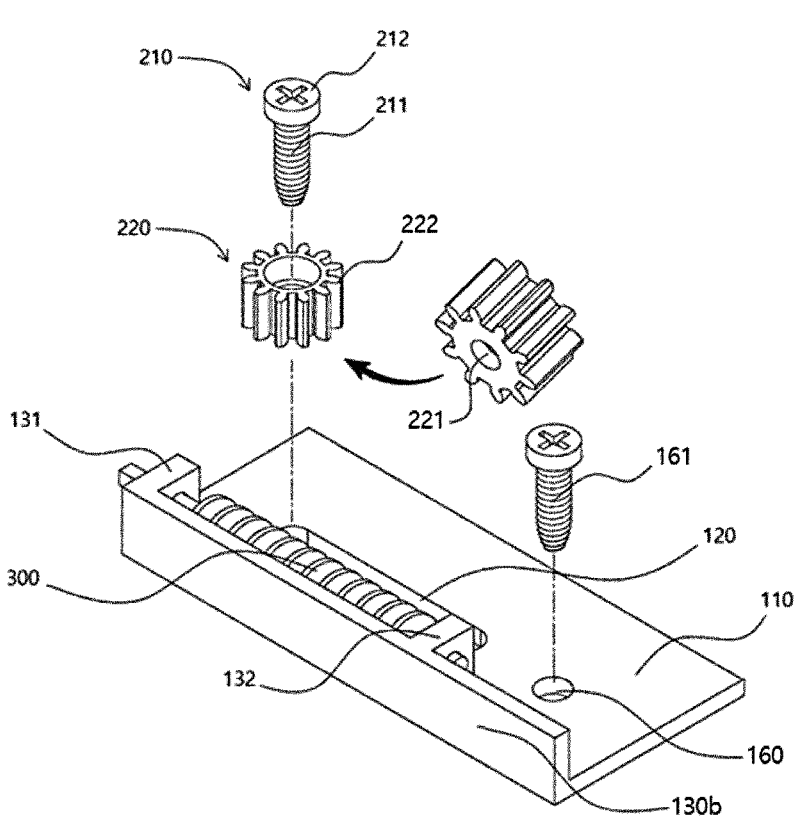
FIG. 13 is an exploded view illustrating the spacing-adjustable bone orthopedic apparatus of FIG. 12.

FIG. 12 is a perspective view illustrating a locking screw engaged with a worm in the spacing-adjustable bone orthopedic apparatus according to the second embodiment of the present invention. FIG. 13 is an exploded view illustrating the spacing-adjustable bone orthopedic apparatus of FIG. 12.

Referring to FIGS. 12 and 13, the spacing-adjustable bone orthopedic apparatus according to the second embodiment of the present invention includes a plate 100, a locking screw 200*b*, and a worm 300.

The plate 100 includes a main body 110, a through portion 120 having a predetermined length and passing through the main body 110, and a first support part 131 and a second support part 132 which are formed to protrude from a bottom surface at one side of the main body 110 and are spaced apart from each other. The plate 100 are disposed across a first bone and a second bone, which are two adjacent bone fragments, one side surface of the main body 110 of the plate 100 is supported by an upper surface of the first bone, and the other side surface thereof is supported by an upper surface of the second bone.

A sidewall 130*b* is formed at one side of the main body 110 in a longitudinal direction of the main body 110 and has a predetermined height. Each of the first support part 131 and the second support part 132 is formed in the form of a wall extending inward from the sidewall 130*b*. The worm 300 is disposed between the sidewall 130*b* and the through portion 120. A distance between the first support part 131 and the second support part 132 is greater than a length of the through portion 120. One end portion of the worm 300 passes through and is supported by the first support part 131, and the other end portion of the worm 300 passes through and is supported by the second support part 132.

The through portion 120 has an elliptical shape formed to extend in the longitudinal direction of the main body 110. One side of the through portion 120 may be disposed on the first bone, and the other side thereof is disposed on the second bone. Alternatively, when a hole is formed outside the through portion 120 to fasten a screw, the through portion 120 may be disposed on only one bone of the first bone and the second bone. A width of the through portion 120 is greater than a diameter of a body portion 211 of a screw body 210 and smaller than a diameter of a head portion 212 of the screw body 210.

The locking screw 200*b* is inserted into the through portion 120. The locking screw 200*b* includes the screw body 210 and the screw head 220 which are capable of being coupled to each other. Outer circumferential surface saw teeth 222 are formed on an outer circumferential surface of the screw head 220. The outer circumferential surface saw teeth 222 are formed along a circumference of the outer circumferential surface of the screw head 220. A hollow having a diameter greater than or equal to the diameter of the head portion 212 of the screw body 210 may be formed in the screw head 220, and the screw body 210 may be inserted into the hollow. In a state in which the screw head 220 is disposed on the through portion 120 and the main body 110 of the plate 100, the screw body 210 passes through the through portion 120 so that an end portion of the screw body 210 is inserted into the first or second bone.

A locking protrusion 221 protruding inward is formed on a portion adjacent to a lowermost side of an inner circumferential surface of the screw head 220. While the screw body 210 is inserted into the first or second bone, a lower side surface of the head portion 212 of the screw body 210 is caught by the locking protrusion 221 of the screw head 220. The locking protrusion 221 extends inward to a length such that the head portion 212 of the screw body 210 is supported and the locking protrusion 221 does not come into contact with an outer circumferential surface of the body portion 211 of the screw body 210. The head portion 212 of the screw body 210 is caught by the locking protrusion 221 and is not inserted further downward.

The worm 300 is supported by the first support part 131 and the second support part 132, and a screw thread that engages with the outer circumferential surface saw teeth 222 of the locking screw 200*b* is formed on the worm 300, wherein the locking screw 200*b* is a worm wheel. The worm 300 is disposed between the sidewall 130*b* and the locking screw 200*b*. The screw thread corresponds to the through portion 120 and is formed in a longitudinal direction of the worm 300 and has a length approximately as long as the through portion 120 extends. The outer circumferential surface saw teeth 222 of the locking screw 200*b* are formed so that the locking screw 200*b* moves according to a preset gear ratio in a longitudinal direction of the through portion 120 when the screw head 200 rotates while engaging with the screw thread of the worm 300. After the locking screw 200*b* moves a predetermined distance, reverse rotation of the screw head 200 of the locking screw 200*b* is prevented by the worm 300, and the screw head 200 is stopped at the position to which it moves.

A motor (not shown) may be connected to one side or the other side of the worm 300. The motor may rotate the worm 300 in one or the other direction. In addition, the motor may be mounted on the plate 100 and designed to be integrated with the plate 100.

Meanwhile, a screw fixing hole 160 spaced apart from the through portion 120 may be formed in the plate 100. In a state in which the plate 100 is fixed to the first or second bone using the screw fixing hole 160 and a fixing screw 161, the locking screw 200*b* may be operated. Accordingly, a fixing force of the plate 100 can increase, and a more stable surgical procedure can be performed.

Figure 14:
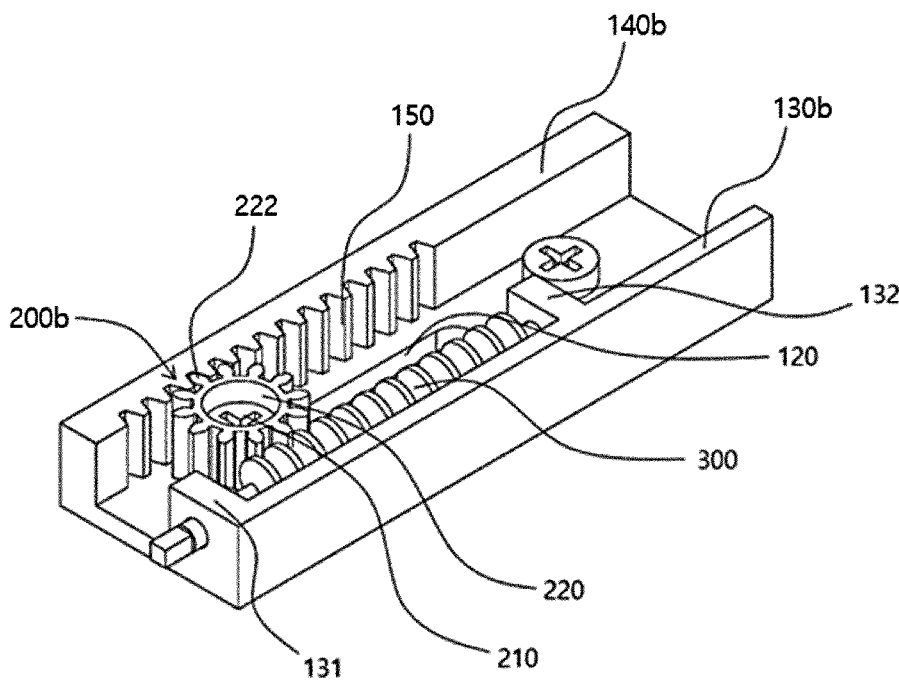
FIG. 14 is a perspective view illustrating a second sidewall provided in the spacing-adjustable bone orthopedic apparatus according to the second embodiment of the present invention.

FIG. 14 is a perspective view illustrating a second sidewall provided in the spacing-adjustable bone orthopedic apparatus according to the second embodiment of the present invention.

Referring to FIG. 14, the spacing-adjustable bone orthopedic apparatus of the present invention may further include a second sidewall 140*b*. A plurality of plate saw teeth 150 that are disposed in front of the worm 300 and engage with the outer circumferential surface saw teeth 222 of the locking screw 200b are formed on the second sidewall 140b in a longitudinal direction. The second sidewall 140b faces the sidewall 130b and is formed at the other side of the plate 100. A distance between the sidewall 130b and the through portion 120 is greater than a distance between the second sidewall 140b and the through portion 120. A distance between the second sidewall 140b and a longitudinal axis of the through portion 120 may be approximately a radius of the screw head 220 of the locking screw 200b. A height of the sidewall 130b and a height of the second sidewall 140b may be approximately a height of the screw head 220.

The plate saw teeth 150 have a length greater than a length of the through portion 120 and are formed to extend in the longitudinal direction of an inner side surface of the second sidewall 140b. The height of the plate saw teeth 150 may be almost the same as a height of the outer circumferential surface saw teeth 222 formed on the outer circumferential surface of the screw head 220.

Figure 15:
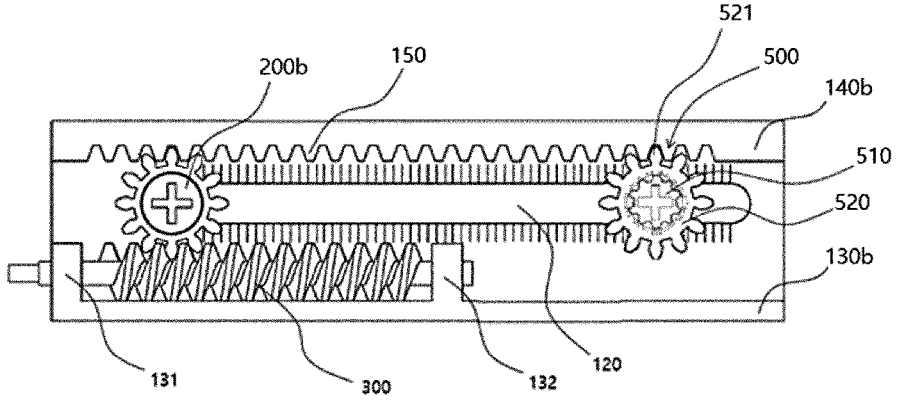
FIG. 15 is a plan view illustrating an application example in which the spacing-adjustable bone orthopedic apparatus of FIG. 14 includes a locking screw and a second locking screw.

FIG. 15 is a plan view illustrating an application example in which the spacing-adjustable bone orthopedic apparatus of FIG. 14 includes the locking screw and a second locking screw.

Referring to FIG. 15, the spacing-adjustable bone orthopedic apparatus according to the second embodiment of the present invention may include the locking screw 200b and a second locking screw 500. The second locking screw 500 is disposed in the through portion 120 to be spaced apart from the locking screw 200b. The structure of the locking screw which is used in the spacing-adjustable bone orthopedic apparatus according to the first embodiment of FIG. 5 and in which locking or locking release is possible may be applied to the second locking screw 500 without change. The locking screw 200b is disposed on the first bone, and the second locking screw 500 is disposed on the second bone.

It is designed that the worm 300 engages with the locking screw 200b, and the worm 300 does not engage with the second locking screw 500. In addition, both the locking screw 200b and the second locking screw 500 are designed to engage with the plate saw teeth 150. In a state in which a position of the second locking screw 500 is fixed with respect to the second bone, when the worm 300 is rotated, the locking screw 200b may be moved toward one side or the other side in the longitudinal direction of the through portion 120 to adjust the movement of the first bone. Meanwhile, in a state in which a position of the locking screw 200b is fixed with respect to the first bone, an operator may move the second locking screw 500 toward one side or the other side in the longitudinal direction of the through portion 120 to adjust the movement of the second bone. Specifically, the operator may rotate a screw head 520 of the second locking screw 500 using a tool or the like after fixing a screw body 510 of the second locking screw 500 to the second bone. Accordingly, outer circumferential surface saw teeth 521 provided on the screw head 520 of the second locking screw 500 engage with the plate saw teeth 150, and the second locking screw 500 is moved.

The scope of the present invention in the art is not limited to the content and description of the embodiment described above. In addition, it is mentioned once again that the scope of the present invention is not limited by obvious changes or substitutions in the art to which the present invention belongs.

REFERENCE NUMERALS

100: PLATE
110: MAIN BODY
111: BODY RACHET SAW TEETH
120: THROUGH PORTION
130A, B: SIDEWALL
131: FIRST SUPPORT PART
132: SECOND SUPPORT PART
140A, B: SECOND SIDEWALL
150: PLATE SAW TEETH
160: SCREW FIXING HOLE
161: FIXING SCREW
200: LOCKING SCREW
200A, B: LOCKING SCREW
210: SCREW BODY
211: BODY PORTION
211A: BODY PORTION SCREW THREAD
212: HEAD PORTION
212A: LOCKING SAW TEETH
212B: INSERTION GROOVE
220: SCREW HEAD
221: LOCKING PROTRUSION
222: OUTER CIRCUMFERENTIAL SURFACE SAW TEETH
223: INNER CIRCUMFERENTIAL SURFACE SAW TEETH
224: HEAD RACHET SAW TEETH
225: ROTATION GROOVE
300: WORM
400: ELASTIC MEMBER
500: SECOND LOCKING SCREW
s1: LOCKING REGION
s2: LOCKING RELEASE REGION

The invention claimed is:

1. A spacing-adjustable bone orthopedic apparatus comprising:
   a plate including a main body and a through portion having a predetermined length and formed to pass through the main body; and
   a locking screw which is inserted into the through portion, which includes a screw body and a screw head which are coupled to each other, and in which outer circumferential surface saw teeth are formed on an outer circumferential surface of the screw head,
   wherein the plate includes a sidewall formed at one side of the main body, and a plurality of plate saw teeth are formed on the sidewall in a longitudinal direction of the sidewall to extend toward the through portion,
   wherein the screw body includes a body portion in which a screw thread is formed on an outer circumferential surface, and a head portion in which locking saw teeth are formed on an outer circumferential surface, and
   wherein the outer circumferential surface saw teeth of the screw head are formed to engage with the plurality of plate saw teeth, and inner circumferential surface saw teeth are formed on a part of an inner circumferential surface of the screw head to engage with the locking saw teeth of the screw body.

2. The spacing-adjustable bone orthopedic apparatus of claim 1, wherein the screw head is disposed on the through portion and supported by an upper surface of the main body of the plate.

3. The spacing-adjustable bone orthopedic apparatus of claim 1, wherein the inner circumferential surface of the screw head includes:
   a locking region in which the inner circumferential surface saw teeth are formed; and
   a locking release region other than the locking region, wherein the locking region is formed to extend inside the inner circumferential surface of the screw head and has a predetermined height.

4. The spacing-adjustable bone orthopedic apparatus of claim 1, wherein:

a locking protrusion protruding inward is formed on a portion adjacent to a lowermost side of the inner circumferential surface of the screw head; and a lower side surface of the head portion of the screw body is caught by the locking protrusion.

5. The spacing-adjustable bone orthopedic apparatus of claim 1, further comprising an elastic member which is disposed between a lower surface of the screw head and the main body and of which one side is inclined toward the lower surface of the screw head.

6. The spacing-adjustable bone orthopedic apparatus of claim 5, wherein the elastic member includes a spring washer.

7. The spacing-adjustable bone orthopedic apparatus of claim 1, further comprising:

head rachet saw teeth formed on a lower side surface of the screw head; and body rachet saw teeth formed on an upper side surface of the main body and corresponding to a shape of the head rachet saw teeth.

8. The spacing-adjustable bone orthopedic apparatus of claim 1, wherein the locking screw includes:

a first locking screw; and a second locking screw disposed in the through portion to be spaced apart from the first locking screw in a longitudinal direction of the through portion.

9. The spacing-adjustable bone orthopedic apparatus of claim 1, wherein a screw fixing hole spaced apart from the through portion is formed in the plate.

10. The spacing-adjustable bone orthopedic apparatus of claim 1, wherein the plate includes a first support part and a second support part which are formed to protrude from a bottom surface at one side of the main body and are spaced apart from each other, wherein the spacing-adjustable bone orthopedic apparatus includes a worm which is supported by the first support part and the second support part and on which a screw thread that engages with the outer circumferential surface saw teeth of the locking screw is formed, and the locking screw is used as a worm wheel.

11. The spacing-adjustable bone orthopedic apparatus of claim 10, wherein:

one end portion of the worm passes through and is supported by the first support part; and the other end portion of the worm passes through and is supported by the second support part.

12. The spacing-adjustable bone orthopedic apparatus of claim 10, further comprising a motor which is connected to the worm and rotates the worm in one direction or the other direction.

13. The spacing-adjustable bone orthopedic apparatus of claim 10, wherein:

the plate further includes a sidewall formed at the other side of the main body; and a plurality of plate saw teeth that are disposed in front of the worm and engage with the outer circumferential surface saw teeth of the locking screw are formed on the sidewall in a longitudinal direction.

14. The spacing-adjustable bone orthopedic apparatus of claim 13, further comprising a second locking screw disposed in the through portion to be spaced apart from the locking screw, wherein the second locking screw engages with the plate saw teeth and moves in a longitudinal direction of the through portion.

\* \* \* \* \*